United States Patent
Xu et al.

(10) Patent No.: US 10,209,216 B2
(45) Date of Patent: Feb. 19, 2019

(54) ELECTROSPRAY IONIZATION SOURCE AND LC-MS INTERFACE

(71) Applicant: BEIJING INSTITUTE OF TECHNOLOGY, Beijing (CN)

(72) Inventors: Wei Xu, Beijing (CN); Zezhen Zhang, Beijing (CN); Muyi He, Beijing (CN); Lili Hu, Beijing (CN)

(73) Assignee: BEIJING INSTITUTE OF TECHNOLOGY, Beijing (CN)

(*) Notice: Subject to any disclaimer, the term of this patent is extended or adjusted under 35 U.S.C. 154(b) by 135 days.

(21) Appl. No.: 15/216,902

(22) Filed: Jul. 22, 2016

(65) Prior Publication Data

US 2017/0025262 A1    Jan. 26, 2017

(30) Foreign Application Priority Data

Jul. 23, 2015  (CN) .......................... 2015 1 0438220

(51) Int. Cl.
*H01J 49/16* (2006.01)
*G01N 27/447* (2006.01)
*G01N 30/72* (2006.01)

(52) U.S. Cl.
CPC ....... *G01N 27/447* (2013.01); *G01N 30/7266* (2013.01); *H01J 49/167* (2013.01)

(58) Field of Classification Search
CPC .... H01J 49/165; H01J 49/167; G01N 27/447; G01N 30/7266
See application file for complete search history.

(56) References Cited

U.S. PATENT DOCUMENTS

| | | | | |
|---|---|---|---|---|
| 5,306,412 A | * | 4/1994 | Whitehouse | B05B 17/0623 204/452 |
| RE34,757 E | * | 10/1994 | Smith | H01J 49/165 204/452 |
| 5,505,832 A | * | 4/1996 | Laukien | G01N 27/44717 204/452 |
| 6,127,680 A | * | 10/2000 | Andrien, Jr. | H01J 49/167 250/281 |
| 6,410,915 B1 | * | 6/2002 | Bateman | H01J 49/0431 250/281 |
| 6,458,597 B1 | * | 10/2002 | Andrien, Jr. | H01J 49/0445 250/281 |
| 7,960,711 B1 | * | 6/2011 | Sheehan | H01J 49/045 250/281 |
| 2002/0139751 A1 | * | 10/2002 | Zhang | B01J 20/3274 210/656 |
| 2005/0258358 A1 | * | 11/2005 | Thakur | H01J 49/04 250/288 |
| 2006/0057556 A1 | * | 3/2006 | Janini | B05B 5/0255 435/4 |

(Continued)

*Primary Examiner* — Nicole M Ippolito
*Assistant Examiner* — Sean M Luck
(74) *Attorney, Agent, or Firm* — Yong Chen

(57) ABSTRACT

The present invention provides an electrospray ionization source, which includes: a capillary, including a spray tip; a first electrode which provides the spray tip with a spray voltage; and a second electrode. The electrical potential difference between the first electrode and the second electrode forms a separation electric field, which allows the electric field separation and electrospray ionization of the sample to be accomplished simultaneously, thereby improving the sensitivity of detection.

17 Claims, 14 Drawing Sheets

(56) References Cited

U.S. PATENT DOCUMENTS

| | | | |
|---|---|---|---|
| 2006/0192107 A1* | 8/2006 | DeVoe | B05B 5/025 |
| | | | 250/288 |
| 2007/0221861 A1* | 9/2007 | Lenke | C07K 1/24 |
| | | | 250/425 |
| 2008/0047330 A1* | 2/2008 | Whitehouse | G01N 30/7266 |
| | | | 73/61.48 |
| 2012/0104248 A1* | 5/2012 | Hardman | H01J 49/165 |
| | | | 250/288 |
| 2014/0014747 A1* | 1/2014 | Moeller | H01J 49/10 |
| | | | 239/690 |

* cited by examiner

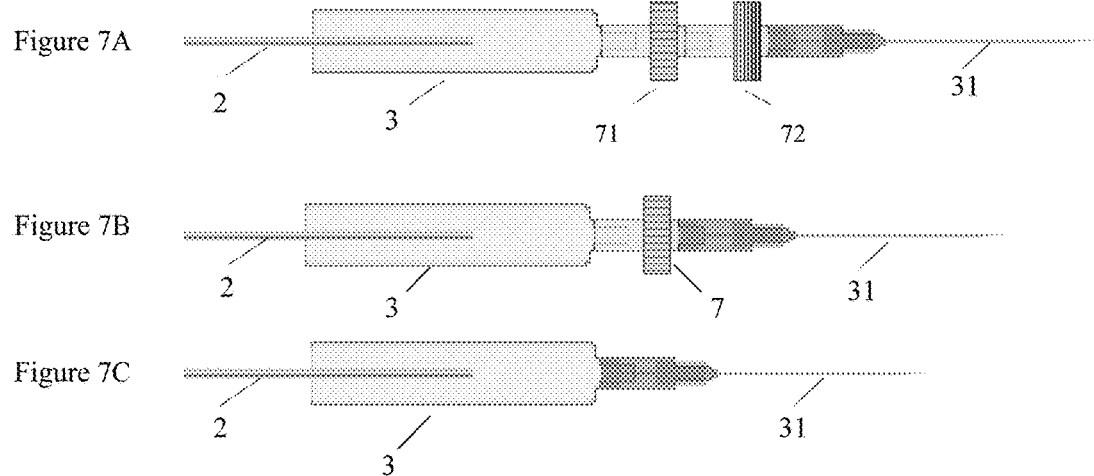

ELECTROSPRAY IONIZATION SOURCE AND LC-MS INTERFACE

CROSS REFERENCE TO RELATED APPLICATION

This application claims priority to Chinese Application No. 201510438220.7, filed Jul. 23, 2015, the disclosure of which is incorporated herein by reference in its entirety.

TECHNICAL FIELD

The present invention relates to an ion source device and a LC-MS interface design, which enables the separation of complex samples in electric field and improves ionization efficiency.

BACKGROUND ART

Mass spectrometry is an analytical method of identifying and characterizing compositions and structures by separating and detecting compounds according to their different mass to charge ratios (m/z). Because of its high specificity and sensitivity, mass spectrometry has an increasingly important role in the field of biological analysis. Bio-mass spectrometry (Bio-MS) is a mass spectrometry technique in the analysis of biomolecules and has been widely used in protein and peptide research, such as protein relative molecular mass determination, peptide mass fingerprinting, peptide sequencing technology, mercapto and disulfide bond localization, protein post-translational modification, quantitative proteome analysis, protein interaction studies, etc. In addition, the bio-mass spectrometry has also been used in structural determination of polysaccharides, oligonucleotides and nucleic acid analysis, microbial identification, drug research and development, and other fields.

The ion source of a mass spectrometer is one of the components that greatly affect the detection sensitivity of the spectrometer. For the detection of a liquid sample, the most common ion source is (nanoliter) electrospray ionization source. The electrospray ionization source uses an electric field to produce charged droplets, which undergo a desolvation process and become analyte ions for mass spectrometry analysis. This process includes three stages: formation of charged droplets, droplets shrinkage, and gas phase ions formation. More recently, nanoliter electrospray ionization source was developed, which greatly reduced the amount of samples required and the flow rate. Electrospray ionization source is widely used in LC-MS interface.

On the other hand, when using electrospray ionization source to detect multi-component samples, ionization competition may occur between the components to be detected, as well as between the to-be-detected components and impurities. Therefore, components with a low abundance and low ionization efficiency may not be detected easily. As a result, in practice, the samples often need to be pre-treated and pre-separated before use. In order to simplify the pretreatment process for complex samples and eliminate the influence of the pretreatment process on the components in this process, the present invention provides improved design over the conventional electrospray method and uses electric field to separate the samples in the ionization process based on their charge property, thereby reducing competition between the components of the sample and improving the ionization efficiency of individual components, and in particular, achieving multi-mode separation in the combination process.

SUMMARY OF THE INVENTION

The present invention provides a novel electrospray ionization source and operating method thereof by adding an auxiliary electric field at the spray capillary, such that separation by the electric field and electrospray ionization of the samples could be accomplished simultaneously.

In one aspect, the present invention provides an electrospray ionization source, comprising: a capillary comprising a spray tip; a first electrode for providing the spray tip of the capillary with a spray voltage; and a second electrode, wherein the electrical potential difference between the first electrode and the second electrode forms a separation electric field.

The distance between the front end of said second electrode and the spray tip of said capillary can be greater than the distance between the front end of said first electrode and the spray tip of said capillary.

Said first and second electrodes can each independently be a linear electrode, an L-shaped electrode, an annular electrode, or a cylindrical sleeve-shaped electrode.

Said first and second electrodes can each independently be a metal electrode, a nonmetal electrode, or a composite material electrode.

The outer surface of said first electrode and/or the second electrode can have an electrically insulating coating.

Either of said first and second electrodes can be in contact with, or not in contact with the sample solution.

Said capillary can be provided with an opening on the side wall, and said first electrode can be disposed at the spray tip portion of said capillary through said opening.

Said capillary can be cut into two or more segments and arranged to form at least one gap between the segments, the first electrode can be disposed at the spray tip portion of said capillary through the gap.

Said first electrode and/or second electrodes can be annular or cylindrical sleeve-shaped electrodes, respectively. Said annular or cylindrical sleeve-shaped electrodes can be placed on the outer surface of said capillary.

Said spray tip can include glass capillary spray tip, metal spray tip, and glass capillary spray tip with metal plating.

The electrospray ionization source can further comprise: DC high voltage source, the output range is 0~+/−20000 V; and/or AC high voltage source, the output voltage range is 0~+/−20000 V, the frequency range is 0~10 kHz.

In another aspect, the present invention provides a LC-MS interface comprising the foregoing electrospray ionization source.

In yet a further aspect, the present invention provides an electrospray ionization source which includes a capillary comprising a metal spray tip providing a spray voltage, and a second electrode, wherein the electrical potential difference between the second electrode and the metal spray tip forms a separation electric field.

Said electrospray ionization source can further comprise: at least one layer of functional membrane being positioned between said metal spray tip and said second electrode.

The electrospray ionization source of the present invention can include two auxiliary electrodes positioned in tandem, where the front electrode provides a spray voltage, and the potential difference between the front and the rear electrodes form a separation electric field. Thus, the ion source of the present invention can produce a separation field before or during the sample ionization process, allowing the electric field separation and electrospray ionization of the sample to be accomplished simultaneously and thereby improving the sensitivity of the electrospray ionization source.

The present invention has the following beneficial effects over the prior art:

1) Separation: samples with different charge properties can be separated by an electric field, indicated by differences in timing of appearance of characteristic peaks, thereby allowing for rapid sample pretreatment;

2) Focusing: for a single component in the sample, such as proteins, peptides with multiple charges, etc., the invention can increase the concentration of the sample in ionization to thereby further improve the detection sensitivity;

3) Retaining the native structure of biological macromolecules in the sample: no pretreatment, e.g., pretreatment that involves adding acid, is needed. Thus, the present invention can protect the native structure of proteins and other molecules;

4) Facilitating the detection of multi-component samples: the present invention reduces the competitive effect in such samples, thereby facilitating detection of the samples with a low abundance or low ionization efficiency.

BRIEF DESCRIPTION OF THE DRAWINGS

FIGS. 7A-7C show structural schematic views of three additional configurations of the electrospray ionization source according to some embodiments of the present invention.

DETAILED DESCRIPTION OF EMBODIMENTS

Figure 1A:
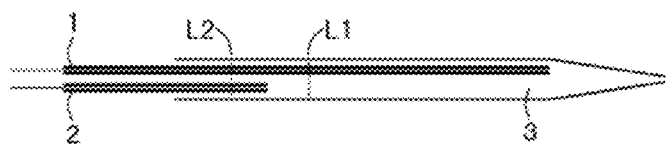
FIGS. 1A-1D show a structural schematic view of four different auxiliary electric fields of certain embodiments of the electrospray ionization source of the present invention.

The examples of the present invention are illustrated below with the aid of the drawings. Elements and features described in one drawing or one embodiment of the present invention may be combined with elements and features described in one or more other drawings or embodiments. It should be noted that for the purpose of clarity, expressions and descriptions of components or processes that are well known to those skilled in this art are omitted from the drawings and statements.

The present invention is further described below with the aid of the drawings.

Electrospray Ionization Source

As shown in FIGS. 1A-1D, the electrospray ionization source comprises a capillary 3 with a spray tip, a first electrode 1, and a second electrode 2.

The electrospray tip may be a glass capillary spray tip, a glass capillary spray tip with metal plating, or a metal spray tip.

With or without contact with the sample solution, the first electrode 1 provides the spray tip of capillary 3 of the electrospray ionization source with a spray voltage. The distance of the front end of the second electrode 2 from the spray tip of the capillary 3 can be greater than the distance of the front end of the first electrode 1 from the spray tip of said capillary 3, that is, the second electrode 2 is disposed in the rear of the first electrode 1 and the second electrode 2 does not provide a spray voltage. The potential difference between the first electrode 1 and the second electrode 2 forms a separation field, which is used to pre-separate the samples in the field. The degree of separation of the samples to be tested depends on the electric field applied by the electrodes and the distance between the electrodes, more particularly, on the length of the separation electric field and the change of the electric field in per unit length, V/cm. An electric field having a greater length or greater change in per unit length is expected to enhance the degree of separation. Those skilled in the art can select the appropriate electric field strength between the first electrode 1 and the second electrode 2 and the arrangement of the two electrodes according to the charged nature of the samples to be tested.

The first electrode 1 and the second electrode 2 may each be linear electrodes, annular electrodes, cylindrical sleeve-shaped electrodes or other shapes. The first electrode 1 and the second electrode 2 may each be selected from metal electrodes, non-metallic electrodes, composite material electrodes, or other electrodes formed from various conducting materials. The outer surface of the first electrode 1 and the second electrode 2 may be provided with an electrically insulating coating. The coating can be an electrically insulating material, so that the voltage exposure points are at the tips of the electrodes 1 and 2, which increase the length of the electric field from the rear to the front, that is, the distance that can form the electric field gradient. Compared with wholly bare electrodes with equal potential and without insulating coatings, this arrange can increase the degree of separation of the samples.

The capillary 3, the first electrode 1 and the second electrode 2 may be arranged in many different configurations. Below are four example configurations to illustrate the concept of the present invention. The present invention is not limited to these examples, and the capillary 3, the first electrode 1 and the second electrode 2 of the present invention may also be arranged in any other configurations that embody the concept of the present invention.

As shown in FIG. 1A, both the first electrode 1 and the second electrode 2 are linear electrodes with electrically insulating coatings. The first electrode 1 and the second electrode 2 are directly inserted into the capillary 3, one in front and the other in the rear. The front end of the first electrode 1 is proximal to the spray tip of the capillary 3 and provides the spray tip with a spray voltage. The front ends of the electrodes 1 and 2 are a certain distance apart, such as one centimeter or more. In other words, as compared with the first electrode 1, the second electrode 2 is further from the spray tip of the capillary 3. In this way, a separation electric field is formed between the first electrode 1 and the second electrode 2.

Figure 1B:
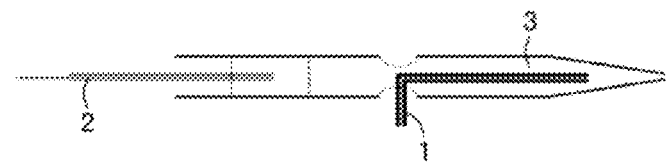

As shown in FIG. 1B, the capillary 3 may be in the form of two segments, the front segment includes a spray tip portion, and the rear segment is a capillary. The first electrode 1 is a L-shaped electrode with an electrically insulating coating, with one leg of the L-shaped electrode being disposed in the front segment of the capillary to provide the spray tip with a spray voltage. The second electrode 2 is a linear electrode that is disposed in the rear segment of the capillary. A separation electric field is formed between the second electrode 2 and the first electrode 1. The front and the rear segments of the capillary can be spaced apart at an appropriate distance to allow the sample solution to form a liquid bridge. The first electrode 1 can be disposed at a distance of, for example, more than 1 cm (from the rear end of the first electrode 1 to the front end of the second electrode 2). The above description is only an example, and the capillary 3 may also include multiple segments.

Figure 1C:
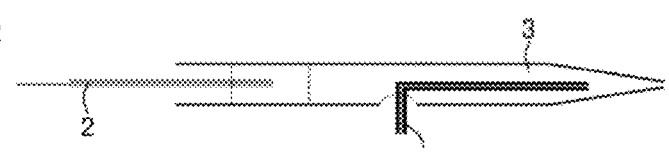

As shown in FIG. 1C, the first electrode 1 is a L-shaped electrode with an electrically insulating coating, while one leg of the L-shaped electrode is disposed in the capillary 3 through a hole that is one centimeter apart from the spray tip of the capillary 3 to provide the spray tip with a spray voltage. The second electrode 2 is a linear electrode that is inserted into the capillary 3 from the rear end. The front end of the second electrode 2 is one centimeter or more apart from the hole. A separation electric field is formed between the second electrode 2 and the first electrode 1.

Figure 1D:
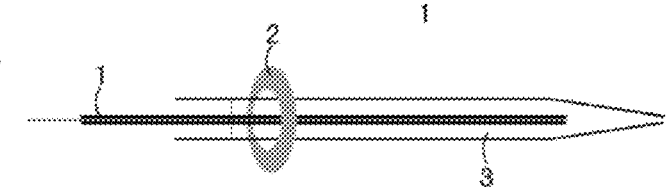

As shown in FIG. 1D, the first electrode 1 is a linear electrode with an electrically insulating coating. The first electrode 1 is directly inserted into the capillary 3, with its front end being proximal to the spray tip of the capillary 3, to provide the spray tip with a spray voltage. The second electrode 2 is an annular electrode. The annular second electrode 2 is placed outside the capillary 3 and spaced from the front end of the first electrode 1 at a certain distance, and the potential difference between the second electrode 2 and the first electrode 1 forms a separation electric field.

Figure 2A:
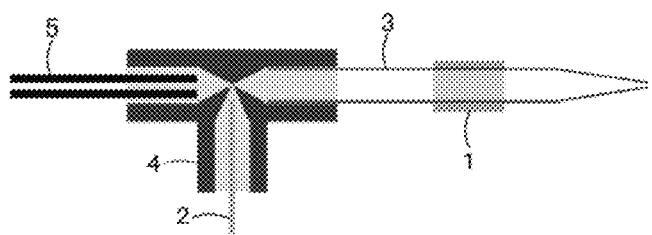
FIGS. 2A-2B show a structural schematic view of two types of LC-MS interfaces according to some embodiments of the present invention.

In the present invention, the first electrode 1 and the second electrode 2 may be in contact, or may not be in contact with the sample solution. As shown in FIGS. 1A-1D, when the liquid surface of the sample solution in the capillary 3 is at the dotted line L1, the second electrode 2 is not in contact with the sample solution; when the liquid surface of the sample solution in the capillary 3 is at the dotted line L2, the second electrode 2 is in contact with the sample solution. As shown in FIG. 2A, the first electrode 1 placed on the outer surface of the capillary 3 is not in contact with the sample solution.

For the spray tip of the capillary 3 of two/multi-segment electrospray ionization source, the sample solutions added to the front and rear segments of the capillary may be the same or different; upon application of an electric field, the sample solution can be added again or added continuously. The sample solution added before and after the application of an electric field may be the same or different.

The first electrode 1 and the second electrode 2 are connected with a high voltage source or grounded, with specific electrical connection depending on the specifics of the mass spectrometer, so as to form a spray voltage and a separation electrical field.

The high voltage source may be a high voltage DC source or a high voltage AC source. The output range of the high voltage DC source is 0~+/−20000 V; the output voltage range of the high voltage AC source is 0~+/−20000 V with a frequency range of 0~10 kHz.

The on-off timing and the strength of the electric field through the two electrodes can be varied, thereby allowing for different modes of operation. A spray voltage can be turned on and off at different times; a separation electric field can be turned on and off at different times; the strength of the electric field being applied may be constant or vary over time.

If the first electrode 1 and the second electrode 2 are simultaneously applied voltages to form a separation electric field, and the voltage of the first electrode 1 is higher than the spray voltage of the sample, the separation/spray can be accomplished simultaneously.

Or, if the first electrode 1 and the second electrode 2 are simultaneously applied voltages to form an electric field, and the voltage of the first electrode 1 is lower than the spray voltage of the sample, a pre-separation of the samples in the electric field can be realized; after a period of time, such as five minutes, the voltage of the second electrode 2 is turned off, and the voltage of the first electrode 1 is increased to be higher than the spray voltage of the sample. In this manner, the operation mode of the pre-separation followed by spray can be realized.

Or, if the first electrode 1 and the second electrode 2 are simultaneously applied voltages to form an electric field, and the voltage of the first electrode 1 is lower than the spray voltage of the sample, a pre-separation of the samples in the electric field can be realized; after a period of time, such as five minutes, the voltages of the first electrode 1 and the second electrode 2 are increased simultaneously to make the voltage of the first electrode 1 higher than the spray voltage of the sample but the electric field strength between the first electrode 1 and the second electrode 2 are maintained constant, the operation mode of the pre-separation followed by simultaneous separation/spray can be realized.

Or, if the first electrode 1 and the second electrode 2 are simultaneously applied a voltage to form a separation electric field, and the voltage of the first electrode 1 is higher than the spray voltage of the sample, a simultaneous separation/spray mode can be realized. The voltage of the second electrode 2 can be changed over time, so that the separation electric field varies over time, which constitutes a changing-field separation/spray mode.

One or more layers of functional membranes may be disposed between the first electrode 1 and the second electrode 2. The functional membranes can be mounted via a bracket.

Functional membranes can be placed in the auxiliary electric field between the first electrode 1 and the second electrode 2. By changing the type and number of layers the functional membranes, different operating modes can be realized. The functional membranes may be one or more layers and may be included or absent. Any combinations of desired membranes can be selected according to molecular size, polarity and other properties, which when coupled with particular mode of sample introduction can accomplish the screening or separation of components from the sample.

For example, the functional membrane can be a porous membrane, which can allow the ions rejected by the porous membrane to be detected preferentially, so that the operation mode of the pre-separation followed by separation/spray can be realized.

Alternatively, the functional membrane can be an inorganic-organic separation membrane. Organic components in the sample can penetrate the membrane, and reach the spray tip at different times based on their respective charge properties, effected by the applied electric field. In this manner, a multi-dimensional separation mode can be realized.

Alternatively, the porous membrane and the inorganic-organic separation membrane are arranged sequentially, the ions having penetrated the porous membrane are then subjected to an organic-inorganic separation. Small organic molecules are detected according to m/z (mass to charge ratio). If the inorganic-organic membrane is removed first, inorganic small molecules are sequentially detected also according to m/z. If the porous membrane is removed, organic large molecules can be detected according to m/z. The electric field also plays a role for separation of components in the process. In this manner, a multi-dimensional separation spray mode can be realized.

The operation modes described above are only some examples of the present invention, rather than all of the modes. The skilled person in the art will understand that the above modes are only intended to illustrate the concepts of the present invention and are not intended to limit the invention.

LC-MS Interface

The present invention relates to a LC-MS interface, that is, an auxiliary electric field is applied at the site of LC-MS interface to allow the electric field separation and electrospray ionization of the sample to be accomplished simultaneously. Specific example designs of the invention are implemented as follows:

An embodiment of the interface utilizing the electrospray ionization source device is shown in FIG. 2A. A cylindrical sleeve-shaped first electrode 1 encircles the outer surface of the spray tip of capillary 3, a high-voltage AC electric field is applied as a spray voltage. A three-way connector 4 is used to connect to the LC outlet 5, the second electrode 2, and the capillary 3. A high voltage DC electric field is applied to the second electrode 2, which is combined with the first electrode 1 to form a separation field.

Figure 2B:
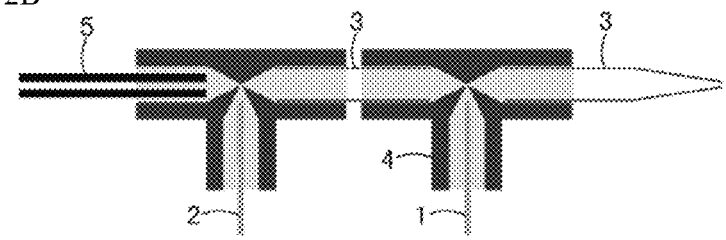

Another embodiment of the interface is shown in FIG. 2B. A three-way connector 4 is used to connect to the first electrode 1, the front segment of the capillary 3 which includes the spray tip, and the rear segment of the capillary 3. A high voltage DC electric field is applied as a spray voltage. A three-way connector 4 is used to connect to the LC outlet 5, the second electrode 2, and the rear segment of capillary 3. A high voltage DC electric field is applied to the second electrode 2, which is combined with the first electrode 1 to form a separation field.

The configurations of the LC-MS interface described above are only some examples of the present invention, rather than all of the configurations. The skilled person in the art will understand that these examples only intended to illustrate the concept of the present invention and are not intended to limit the present invention.

The present invention is illustrated by the following examples. Samples used in these examples include: cytochrome C (95%, SDS-PAGE), angiotensin I (HPLC grade), formic acid (HPLC grade) purchased from Sigma-Aldrich (USA); methanol (HPLC grade) purchased from Fisher Scientific (USA); pure water purchased Wahaha Group. The instruments used include: ion trap mass spectrometer (HCT Ultra PTM Discovery System, Bruker, Germany), electronic balance (AR2140, OHAUS Corp., USA), centrifuge (Biofuge 22R, Heraeus Sepatech Inc., Germany), etc.

Example 1

The sample tested in this Example was cytochrome C.

10 mg of cytochrome C powder was dissolved in 10 ml of methanol/water (1:1) solvent to prepare a base solution, methanol/water (1:1) solvent was used to dilute the base solution until the sample had a final concentration of 0.1 mg/ml. A capillary 3 with a spray tip was cut into two segments with a glass knife. The front segment of the capillary glass tube plus the spray tip were about 2 cm long, the rear segment of the capillary was about 5 cm long. The first segment was filled with the sample, and inserted therein a L-shaped electrode with an electrically insulating layer as the first electrode 1, which was grounded. The rear segment of the capillary was aligned with the front segment with respect to their respective cut ends, and was placed on a fixed bracket. An amount of sample was slowly added into the front segment, forming a liquid bridge at the gap between the cut ends (which was about 2 mm) and extending for about 5 mm into the rear segment of the capillary. An electrode with an electrically insulating layer as the second electrode 2 was inserted from the rear end of the rear segment of the capillary 3. The front end of the second electrode 2 was 1.5 cm apart from the rear sample liquid surface, and connected to the cathode of a high-voltage DC power output. The spray tip of the capillary 3 was aligned to the inlet of a mass spectrometer, and the high-voltage DC output power supply −8000 V was switched on. The MS cone voltage was set at −1000 V to start a spray test.

FIGS. 3A-3E show the results of using the electrospray ionization source of the present example as compared with a currently available (conventional) electrospray ionization source to detect a single sample.

Figure 3A:
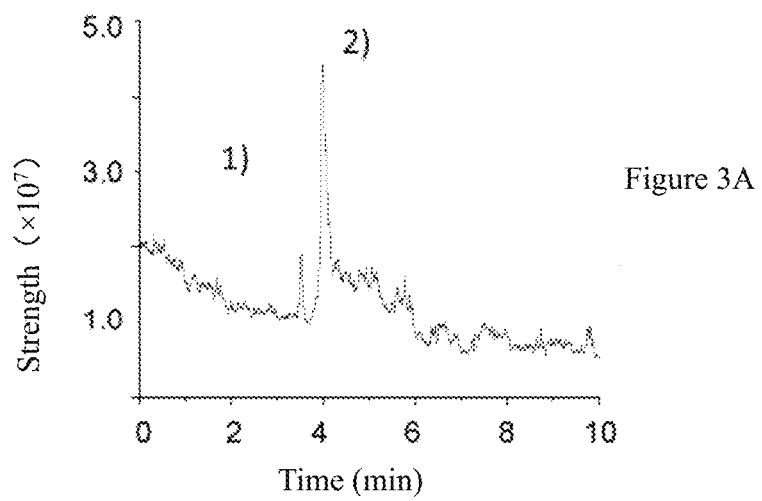
FIGS. 3A-3E show comparison diagrams for detecting a single sample using an embodiment of electrospray ionization source of the present invention and a currently available electrospray ionization source.

FIG. 3A is a total ion stream diagram of cytochrome C detected by using the electrospray ionization source of the present example. As can be seen from the figure, after three minutes the total ion stream begins to increase, the peaks for cytochrome C appear. The curves are divided into two stages: stage 1) corresponds to the pre-peak ion stream, and stage 2) corresponds to the after-peak ion stream.

Figure 3B:
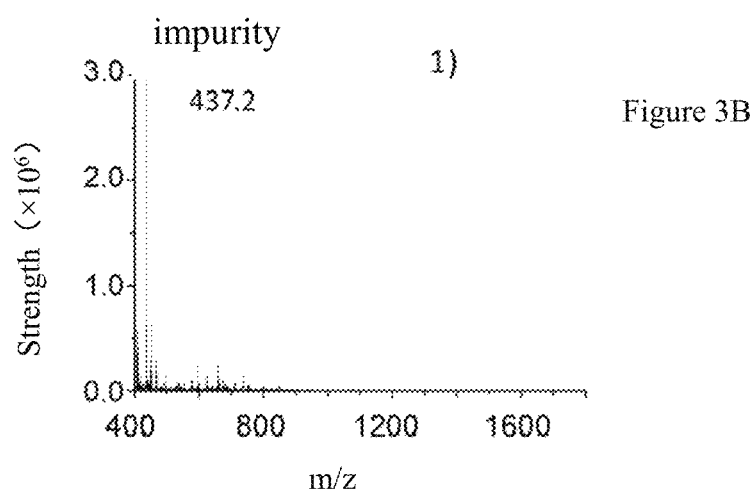

FIG. 3B is a mass spectrum of stage 1) of FIG. 3A, where only impurities can be seen at m/z of 437.2, but no characteristic peaks of cytochrome C was observed.

Figure 3C:
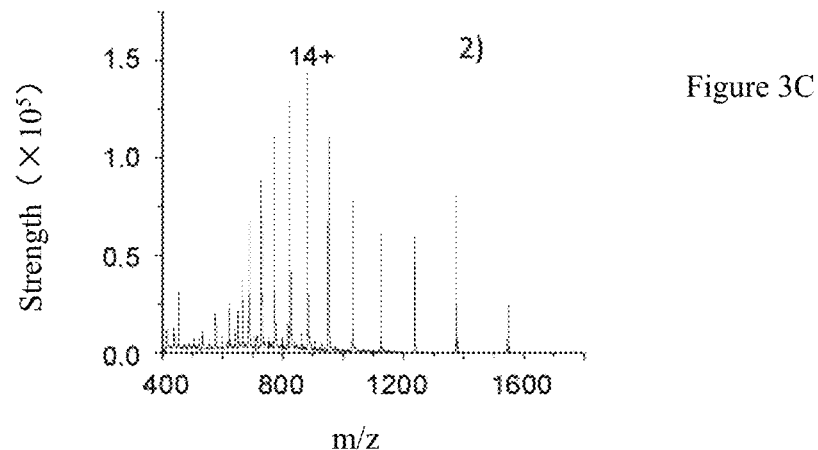

FIG. 3C is a mass spectrum of stage 2) of FIG. 3A, where a cluster of protein peaks of cytochrome C can be observed.

Figure 3D:
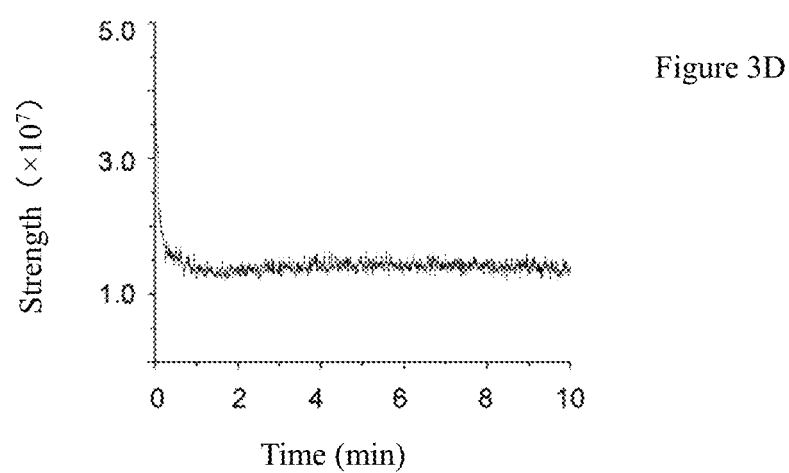

FIG. 3D is a total ion stream diagram by using a currently available nanoliter electrospray ionization source to detect cytochrome C. As can be seen in the recording of 10 minutes, no characteristic peaks appear.

Figure 3E:
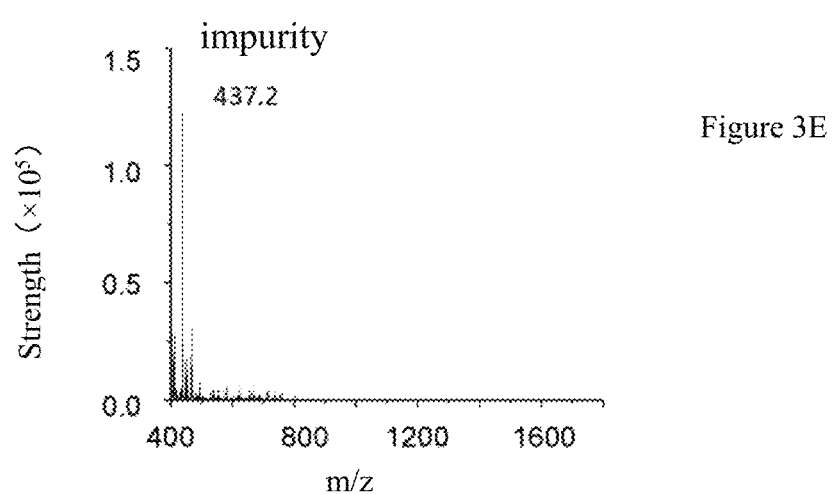

FIG. 3E is a mass spectrum by using a currently available nanoliter electrospray method. Within the detection time, no peaks of cytochrome C are detected.

From the above, it can be seen that the use of electrospray ionization source device of the present example to detect a single sample can effectively improve the sensitivity of detection.

Example 2

The sample tested in this Example was a mixed sample of Rhodamine B, angiotensin I and cytochrome C.

Methanol/water (1:1) as a solvent were used to dilute the base solution of three base solutions to formulate a mixed sample with final concentrations of Rhodamine B of 1 ppm, angiotensin I of 1 ppm, and cytochrome C of 50 ppm. In the same manner as described in Example 1, the mixed sample was slowly added to the front segment capillary to extend the liquid surface in the rear segment capillary about 4 mm from a liquid bridge. The second electrode 2 was not in contact with the liquid of the sample and was about 1.5 cm apart from the rear liquid surface. The first electrode 1 was grounded, and the second electrode 2 was powered at −8000 V. The mass spectrometer cone voltage was set at −1000 V. Then the recording was started.

FIGS. 4A-4G show the results of using the electrospray ionization source of the present example and currently available electrospray ionization source to detect the mixed sample.

Figure 4A:
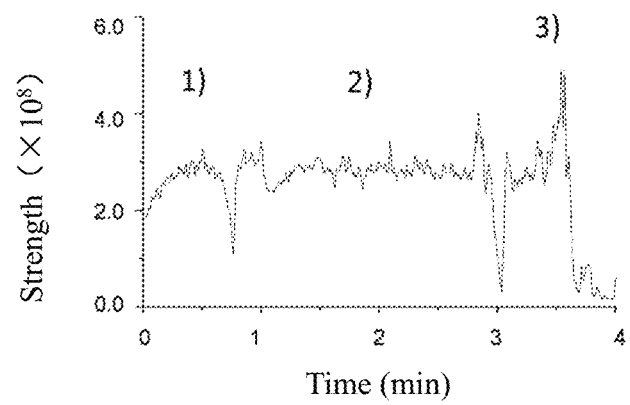
FIGS. 4A-4G show comparison diagrams for detecting mixed samples by using an embodiment of electrospray source of the present invention and a currently available electrospray ionization source.

FIG. 4A is a total ion stream diagram by using the electrospray ionization source of the present example to detect the mixed sample. As can be seen that there are three time stages.

Figure 4B:
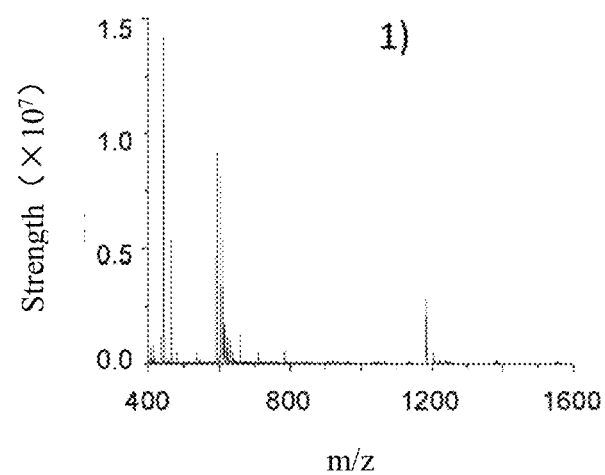
Figure 4C:
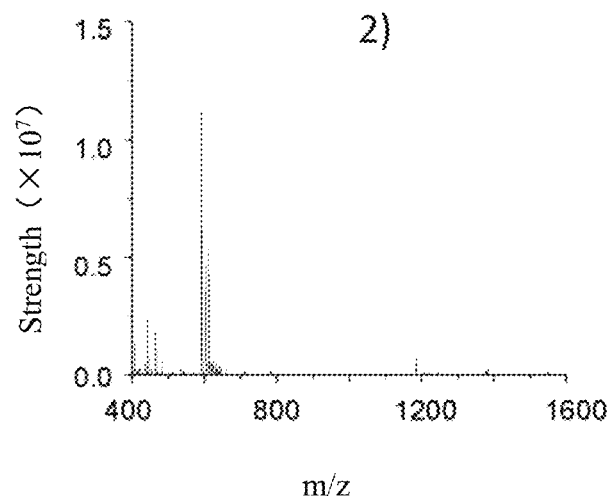
Figure 4D:
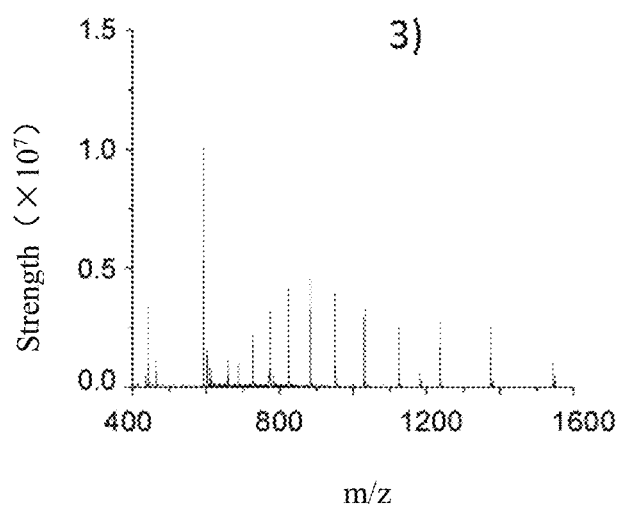
Figure 4E:
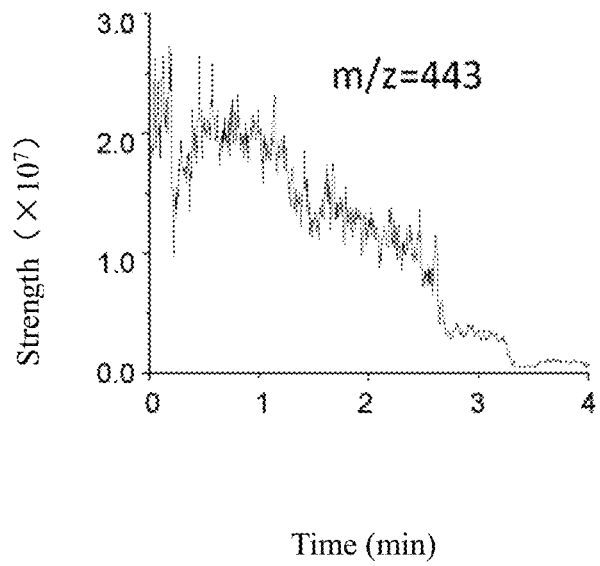
Figure 4F:
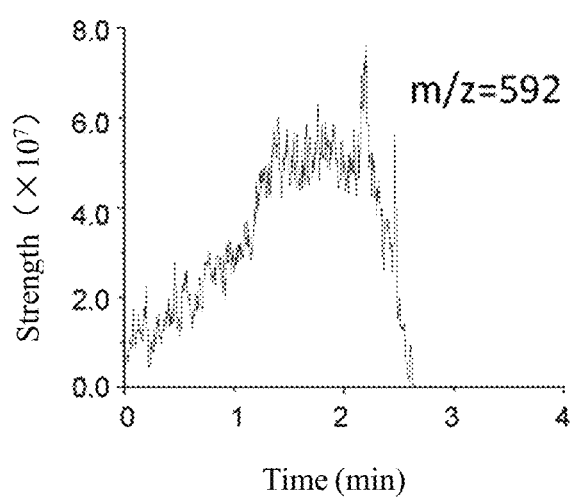
Figure 4G:
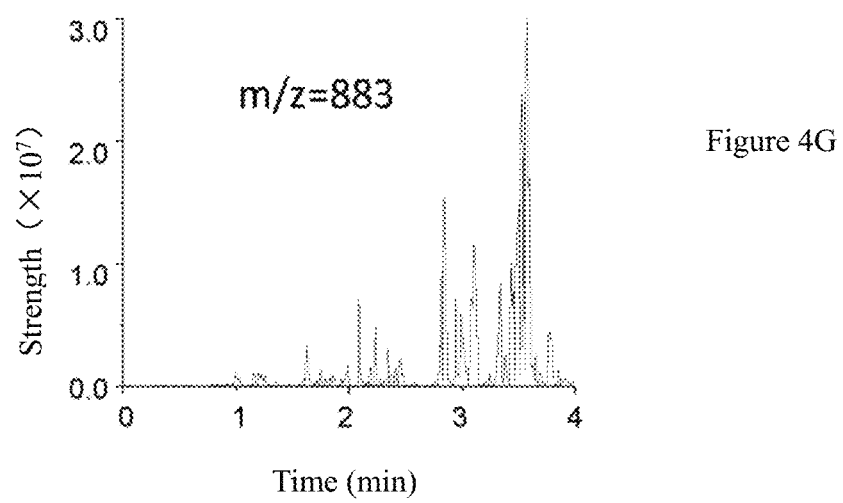

FIGS. 4E-4G correspond to ion stream diagrams of characteristic peaks of three components of Rhodamine B, angiotensin I and cytochrome C, respectively, wherein 14 positive charge peaks (mass to charge ratio of 883) were chosen as characteristic peaks of cytochrome C to monitor the change of the ion stream. The order of appearance of the three components can be seen.

In view of FIGS. 4E-4G the following information can be seen from FIGS. 4B-4D. FIG. 4B shows the peaks appearing in stage 1). It can be seen within one minute from the start of the test, the Rhodamine B peak (m/z 443) is quite strong, and no peaks of protein appear. FIG. 4C shows the peaks appearing in the stage 2), where it can be seen that in this stage, the peak signal strengths of angiotensin I (mass to charge ratio is 592) are greater than those of Rhodamine B. FIG. 4D shows the peaks appearing in the stage 3), where it can be seen that a cluster of cytochrome C protein peaks appear, while the peak strengths of both Rhodamine B and angiotensin I decrease.

Referring again to FIGS. 4A-4G, the LC-MS interface of the present example is used to detect a mixed sample of Rhodamine B, angiotensin I and cytochrome C. Within the first minute from the start of the test, Rhodamine B has the strongest signal, and angiotensin I has a gradually increasing strength which exceeds the signal strength of Rhodamine B after 1 minute. After 3 minutes, a cluster of protein peaks of cytochrome C appears and the strengths of Rhodamine B and the angiotensin I decrease. After the chromatograms of the three samples are extracted, it can be seen that the order of appearances of the peaks is small molecule Rhodamine B, then short peptide angiotensin I, and finally protein cytochrome C. The foregoing demonstrated that when the electrospray ionization source device of the present example is used to detect the mixed sample, the process of pretreating the complex sample is simplified and the detection sensitivity is effectively improved.

Example 3

The sample tested in this Example was cytochrome C.

Since the ionization of proteins is not as easy as other small molecules, during nanoliter electrospray, an acid pretreatment is often required. A currently available nanoliter electrospray ionization source (as control) was used to add 20 ppm of sample to 0.1% formic acid, and the currently available nanoliter electrospray ionization source was used to obtain protein peaks of the cytochrome C. The test results were shown in FIG. 5B.

As a comparison, in this example, cytochrome C with a final concentration of 20 ppm, without pretreatment, was tested using the method described in Example 1, where the first electrode 1 was grounded, the second electrode 2 was under voltage of −9000 V, cone voltage of the mass spectrometer was set at −1000 V, and the protein peaks of cytochrome C were obtained in about 2 minutes. The test results were shown in FIG. 5A.

Figure 5A:
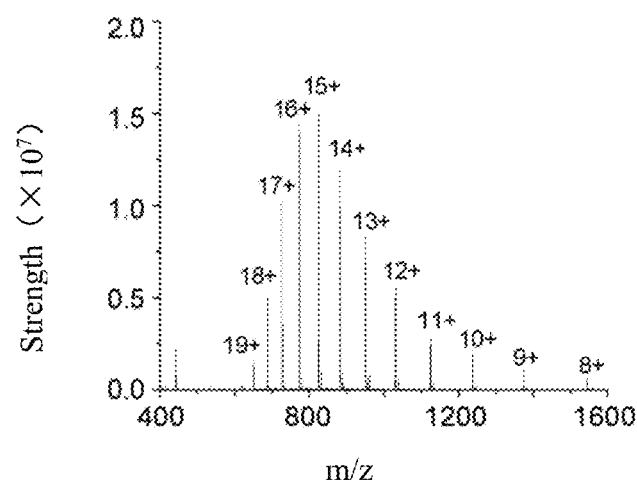
FIGS. 5A-5C show comparison diagrams of using the electrospray ionization source of the present invention to detect a single sample vs. using a currently available electrospray ionization source to detect proteins after acid pretreatment.

FIG. 5A shows mass spectra of cytochrome C protein obtained using the electrospray ionization source of the present example.

Figure 5B:
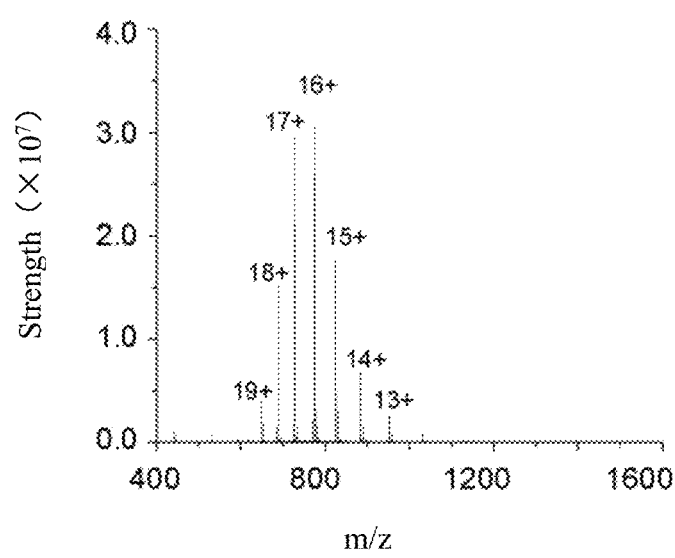

FIG. 5B shows mass spectra of cytochrome C protein obtained using a currently available nanoliter electrospray ionization source after an acid pretreatment.

Figure 5C:
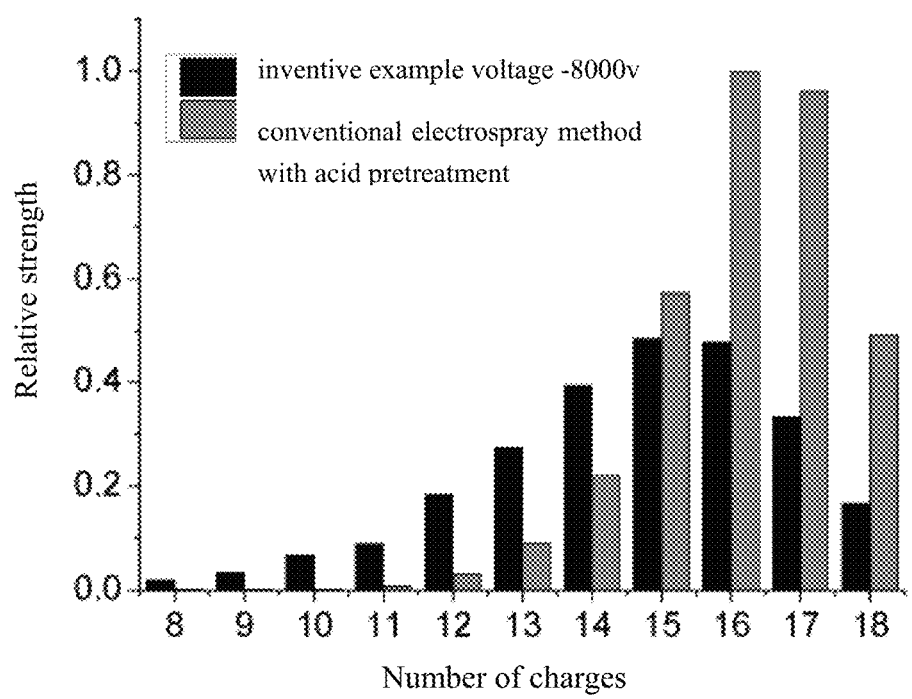

FIG. 5C shows a comparison diagram of protein peak charge distribution and signal response using the electrospray ionization source of the present example vs. using a currently available electrospray ionization source.

The protein test results obtained using the electrospray ionization source device of the present example show a wider protein peak charge distribution which corresponds to a more complete protein structure. In contrast, the protein test results obtained by using a currently available nanoliter electrospray ionization source with acid pretreatment show an increased signal strength, but more charged proteins and significant structural change from its native state.

Example 4

The sample used in this Example were mononuclear macrophages.

Sample cells were cultured by using a mixture of 1640 culture solution and bovine serum 9:1 plus 1% of Penicillin-Streptomycin for about 3 days. Two dish cells were taken and centrifuged. 200 microliters of methanol/water (1:1) was added to the cell pellet obtained. Cell lysates were obtained from the supernatant after sonication and centrifugation. The number of cultured cells in two bottles was approximately 3.67 million. The resulting cell lysates were subjected to the method as described in Example 1, wherein the first electrode 1 was grounded, voltage −9000 v was applied to the second electrode 2, the mass spectrometer cone voltage was set at −1100 v. The results were compared with those obtained by using a currently available nanoliter electrospray ionization source (with and without acid treatment). The test results are shown in FIGS. 6A-6F.

Figure 6A:
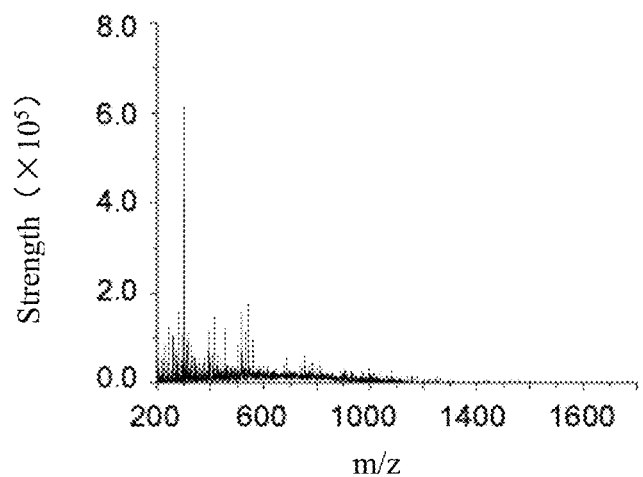
FIGS. 6A-6F show comparison diagrams obtained by using (1) an embodiment of electrospray ionization source of the present invention, (2) currently available nanoliter electrospray ionization source, and (3) currently available nanoliter electrospray ionization source with acid pretreatment, in detecting complex cell samples.
Figure 6B:
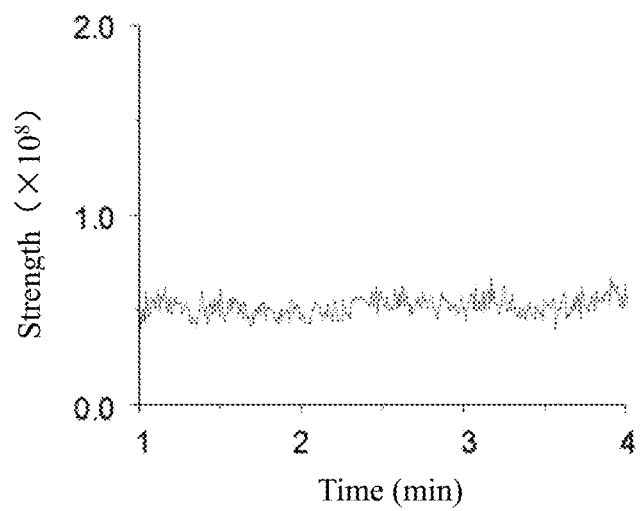
Figures 6C, 6D:
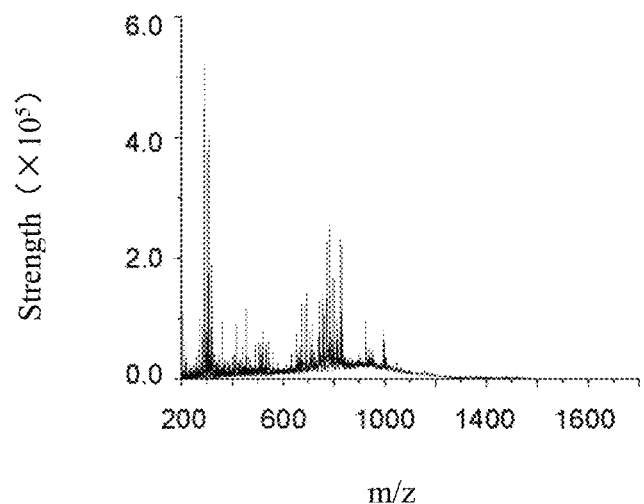
Figure 6E:
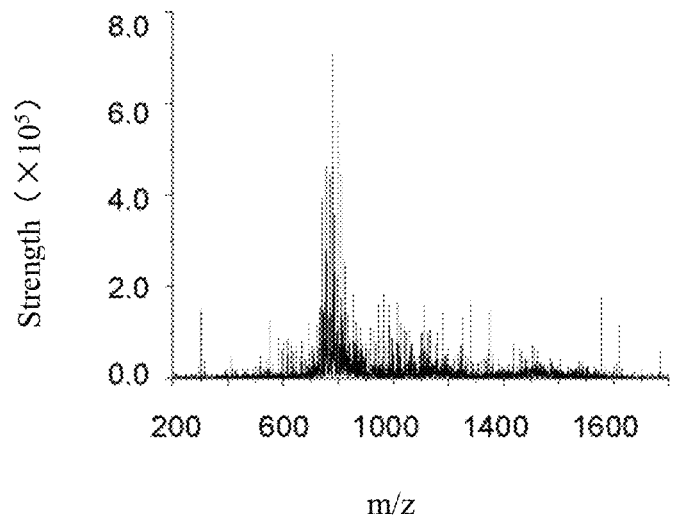
Figure 6F:
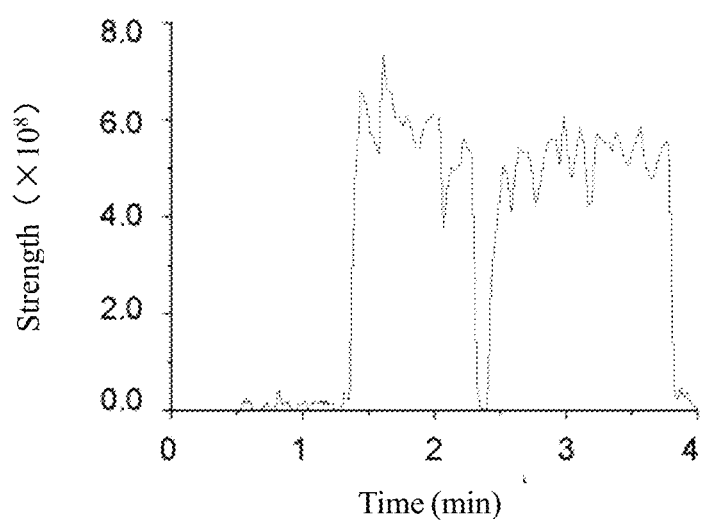

FIGS. 6A-6B show peak conditions and total ion stream diagrams by using a currently available nanoliter electrospray ionization source to the mononuclear macrophage lysates. It can be seen from the figure, for a complex biological sample that has not been processed, only low-mass impurities appear on the spectrum, the total ion stream is stable and has a low strength. FIGS. 6C-6D show peak conditions and total ion stream diagrams by applying currently available nanoliter electrospray ionization source to the mononuclear macrophage lysates with 0.1% formic acid added. It can be seen from the figure, for a complex biological sample without any processing, medium-quality biomass characteristic peaks appear on the spectrum, the total ion stream is stable and has a stronger strength than that of FIGS. 6A-6B. FIGS. 6E-6F show peak conditions and total ion stream diagrams when using the electrospray ionization source of the present example to the mononuclear macrophage lysates. It can be seen from the figure, for a complex biological sample processed by the method of the present example, high mass-end biomass characteristic peaks appear on the spectrum, the total ion stream shows a chromatogram-like peak appearing process. In FIG. 6F, the ion strength increases during 1.3-4 min and is stronger than those obtained using the previous methods.

The present invention also provides an electrospray ionization source, as shown in FIGS. 7A-7C, which includes a capillary 3, a second electrode 2, and a functional membrane 7. The capillary 3 includes a metal electrospray tip 31, which is connected to the power supply to provide the spray voltage. The potential difference between the second electrode 2 and the metal electrospray tip 31 forms a separation electric field. One or more layers of functional membranes 7 can be disposed between the metal electrospray tip 31 and the second electrode 2 and the functional membranes 7 are fixed via a bracket.

As shown in FIG. 7A, the metal electrospray tip 31 instead of the first electrode 1 supplies a spray voltage, the second electrode 2 is inserted from the rear end of the capillary 3, and two layers of functional membranes 71 and 72 are disposed between the metal electrospray tip 31 and the second electrode 2. The functional membranes and the bracket are located between the metal electrospray tip 31 and the second electrode 2, the electric field and the functional membranes can realize multi-dimensional separation of the sample. After switching on power and setting parameters of the mass spectrometer, a spray testing can be performed.

As shown in FIG. 7B, the metal electrospray tip 31 instead of the first electrode 1 supplies spray voltage, the second electrode 2 is inserted from the rear end of the capillary 3, and one layer of functional membrane 7 is disposed therebetween.

As shown in FIG. 7C, the metal electrospray tip 31 instead of the first electrode 1 supplies a spray voltage, the second electrode 2 is inserted from the rear end of the capillary 3, and no functional membrane 7 is disposed.

By using the metal spray electrospray tip 31 to supply a voltage, the interface structure is simplified. The added functional membranes in combination with the electric field allow for multi-dimensional separation of the samples, which purifies the sample and improve the detection effectiveness.

Different types and number of layers of functional membranes can be added in the auxiliary electric field between the metal electrospray tip 31 and the second electrode 2 to realize different operating modes. The functional membranes may be one or more layers, and may be incorporated or removed, it is possible to select any combinations of desired membranes according to molecular size, polarity and other properties, which when coupled with particular mode of sample introduction, the screening or separation of components from the sample can be realized.

For example, the functional membrane can be a porous membrane, which allows the ions rejected by the porous membrane to be detected preferentially, so that the operation mode of pre-separation followed by separation/spray can be achieved.

Alternatively, the functional membrane can be an organic-inorganic separation membrane that separates organics from inorganic material. Organic components in the sample can penetrate the membrane and will reach the spray tip at different times based on their respective charge properties, effected by the applied electric field. In this manner, a multi-dimensional separation mode can be realized.

Alternatively, the porous membrane and the organic-inorganic separation membrane can be arranged sequentially, the ions having penetrated the porous membrane are then subjected to an organic-inorganic separation. Small organic molecules are detected according to m/z (mass to charge ratio). If the organic-inorganic separation membrane is removed first, inorganic small molecules are sequentially detected also according to m/z. If the porous membrane is removed, organic large molecules can be detected according to m/z. The electric field also plays a role for separation of the components in the process. In this manner, a multi-dimensional separation spray mode can be realized.

Although the invention and its advantages have been described in detail, it should be understood that without departing from the spirit and scope of the appended claims as defined in the present invention that various modifications, substitutions and changes can be made. Moreover, the scope of the present application is not limited to the specific examples of processes, systems, devices, methods and steps described in the specification. A person skilled in the art based on the disclosure of the present invention will readily understand that in accordance with the present invention they can use processes, systems, devices, methods and steps to implement similar functions as the corresponding examples described herein or obtain similar results. Therefore, the appended claims intend to include such processes, systems, devices, methods and steps within their scope.

What is claimed is:

1. An electrospray ionization source comprising:
    a capillary comprising a spray tip, wherein the capillary having an elongated body defining a longitudinal direction;
    a first electrode providing the spray tip of the capillary with a spray voltage; and
    a second electrode, wherein the electrical potential difference between the first electrode and the second electrode forms a separation electric field,
    wherein said first electrode and second electrode each has a front end, and wherein the distance of the front end of said second electrode from the spray tip of said capillary along the longitudinal direction is greater than the distance of the front end of said first electrode from the spray tip of said capillary along the longitudinal direction,
    wherein the front end of the second electrode does not extend beyond the spray tip and is spaced apart from the spray tip along the longitudinal direction, and
    wherein said capillary includes an opening on a side wall, and said first electrode includes a first portion and a second portion, the first portion disposed inside the capillary along the longitudinal direction, and the second portion passing through the side opening.

2. The electrospray ionization source according to claim 1, wherein said first electrode is selected from the group consisting of a metal electrode, and a composite material electrode.

3. The electrospray ionization source according to claim 1, wherein either or both said first electrode and the second electrodes have an outer surface with an insulating coating.

4. The electrospray ionization source according to claim 1, wherein at least a portion of the second electrode is disposed inside the capillary.

5. The electrospray ionization source according to claim 1, wherein the opening takes the form of a gap between two segments of said capillary.

6. The electrospray ionization source according to claim 1, wherein the second electrode is annular or cylindrical in shape and is placed on an outer surface of said capillary.

7. The electrospray ionization source according to claim 1, wherein said spray tip is selected from the group consisting of
    a glass capillary spray tip, a metal spray tip, and a glass capillary spray tip with metal plating.

8. The electrospray ionization source according to claim 1, further comprising at least one of:
    a high voltage DC source having an output voltage range of between 0 and +/−20000V; and a high voltage AC source having an output voltage range of between 0 and +/−20000V, and having a frequency range of between 0 and 10 kHz.

9. An LC-MS interface, comprising:
the electrospray ionization source according to claim 1.

10. The electrospray ionization source according to claim 1, wherein said spray tip is metal, the electrospray ionization source further comprising:
at least one layer of functional membrane, the functional membrane being positioned between said metal spray tip and said second electrode.

11. The electrospray ionization source according to claim 1, wherein said first electrode is a nonmetal electrode.

12. The electrospray ionization source according to claim 1, wherein said second electrode is selected from the group consisting of a metal electrode and a composite material electrode.

13. The electrospray ionization source according to claim 1, wherein said second electrode is a nonmetal electrode.

14. The electrospray ionization source according to claim 1, wherein the second electrode is disposed outside the capillary.

15. The electrospray ionization source according to claim 1, wherein the second electrode is disposed entirely at the rear of the first electrode in the longitudinal direction.

16. The electrospray ionization source according to claim 1, wherein the first portion and the second portion of the first electrode form an L-shape.

17. The LC-MS interface according to claim 9, further comprising a three-way connector that couples an LC outlet and the capillary, wherein the second electrode is disposed in a side opening of the three-way connector.

\* \* \* \* \*